US012691198B2

(12) United States Patent
Hoyas

(10) Patent No.: US 12,691,198 B2
(45) Date of Patent: Jul. 28, 2026

(54) NON-WOVEN OF SPUNBONDED THERMOPLASTIC FILAMENTS HAVING IMPROVED WELDABILITY PROPERTIES AND METHOD FOR MANUFACTURING SUCH A NON-WOVEN

(71) Applicant: DOUNOR, SAS, Neuville en Ferrain (FR)

(72) Inventor: Stéphanie Hoyas, Tourcoing (FR)

(73) Assignee: DOUNOR, SAS, Neuville en Ferrain (FR)

( * ) Notice: Subject to any disclaimer, the term of this patent is extended or adjusted under 35 U.S.C. 154(b) by 810 days.

(21) Appl. No.: 14/074,755

(22) Filed: Nov. 8, 2013

(65) Prior Publication Data

US 2014/0135725 A1 May 15, 2014

(30) Foreign Application Priority Data

Nov. 15, 2012 (FR) ...................................... 12 60877

(51) Int. Cl.
| | |
|---|---|
| *A61L 15/42* | (2006.01) |
| *A61F 13/15* | (2006.01) |

(Continued)

(52) U.S. Cl.
CPC ........ *A61L 15/42* (2013.01); *A61F 13/15658* (2013.01); *A61F 13/15756* (2013.01); *A61F 13/4963* (2013.01); *A61F 13/51401* (2013.01); *A61F 13/515* (2013.01); *A61F 13/5633* (2013.01); *A61F 13/565* (2013.01); *A61L 15/24* (2013.01); *B29C 48/0011* (2019.02); *B29C 48/002* (2019.02); *B29C 48/0021* (2019.02); *B29C 48/05* (2019.02); *B32B 5/022* (2013.01);

(Continued)

(58) Field of Classification Search
CPC ....................................................... A61L 15/42
USPC .......................................................... 442/392
See application file for complete search history.

(56) References Cited

U.S. PATENT DOCUMENTS

| | | | |
|---|---|---|---|
| 5,629,080 A | 5/1997 | Gupta et al. | |
| 6,649,548 B1 | 11/2003 | Shawver | |

(Continued)

FOREIGN PATENT DOCUMENTS

| | | | |
|---|---|---|---|
| EP | 2028296 B1 | 2/2012 | |
| WO | WO 2009027021 A2 * | 3/2009 | .............. C08L 23/10 |

OTHER PUBLICATIONS

Translation for WO 2009/027021 to Schlag.*
Conversion for decigrams per minute to grams per 10 minute found at google.com retrieved on Sep. 1, 2020. (Year: 2020).*

*Primary Examiner* — Peter Y Choi
(74) *Attorney, Agent, or Firm* — BURR & FORMAN

(57) ABSTRACT

The object of the present disclosure is a non-woven of spunbonded thermoplastic filaments comprising in a characteristic way, at least 95% by mass (g) of its surface mass (g/m²) of at least two polypropylene A and B polymers, said filaments having a titer of less than or equal to 1.3 dtex, said non-woven having a surface mass of less than or equal to 35 g/m², the welding rate being at least 10% and at most 25% and at least 88% by mass (g) of its surface mass (g/m²) of said polypropylene A polymer obtained by polymerization in the presence of at least one polymerization catalyst based on a metallocene and at most 12% by mass (g) of its surface mass of said polypropylene B polymer.

18 Claims, 2 Drawing Sheets

(51) Int. Cl.

| | |
|---|---|
| *A61F 13/496* | (2006.01) |
| *A61F 13/514* | (2006.01) |
| *A61F 13/515* | (2006.01) |
| *A61F 13/56* | (2006.01) |
| *A61L 15/24* | (2006.01) |
| *B29C 48/00* | (2019.01) |
| *B29C 48/05* | (2019.01) |
| *B32B 5/02* | (2006.01) |
| *B32B 5/26* | (2006.01) |
| *D01D 5/098* | (2006.01) |
| *D01F 6/46* | (2006.01) |
| *D04H 3/007* | (2012.01) |
| *D04H 3/16* | (2006.01) |

(52) U.S. Cl.
CPC ............. *B32B 5/26* (2013.01); *D01D 5/0985* (2013.01); *D01F 6/46* (2013.01); *D04H 3/007* (2013.01); *D04H 3/16* (2013.01); *A61F 2013/51452* (2013.01); *B32B 2262/0253* (2013.01); *B32B 2307/54* (2013.01); *B32B 2307/726* (2013.01); *B32B 2555/02* (2013.01); *Y10T 156/10* (2015.01); *Y10T 442/671* (2015.04)

(56) References Cited

U.S. PATENT DOCUMENTS

| | | | | |
|---|---|---|---|---|
| 2003/0022582 | A1* | 1/2003 | Cree | ....................... B32B 25/10 |
| | | | | 442/394 |
| 2003/0118818 | A1* | 6/2003 | Demain | .................... D01F 6/06 |
| | | | | 428/395 |
| 2005/0130544 | A1* | 6/2005 | Cheng | .................... B32B 5/022 |
| | | | | 442/415 |
| 2005/0165173 | A1 | 7/2005 | Autran et al. | |
| 2005/0196630 | A1 | 9/2005 | Carper et al. | |
| 2007/0287813 | A1* | 12/2007 | Meverden | ............. C08F 110/06 |
| | | | | 526/125.3 |
| 2008/0182940 | A1* | 7/2008 | Dharmarajan | ......... D04H 1/544 |
| | | | | 525/240 |
| 2009/0111347 | A1 | 4/2009 | Peng et al. | |
| 2009/0233073 | A1* | 9/2009 | Bornemann | ........... D04H 13/00 |
| | | | | 442/361 |
| 2009/0233510 | A1* | 9/2009 | Bornermann | ............. B32B 5/26 |
| | | | | 442/361 |
| 2010/0228214 | A1 | 9/2010 | Bornemann et al. | |
| 2011/0059668 | A1 | 3/2011 | Bieser et al. | |
| 2012/0179125 | A1 | 7/2012 | Kanya et al. | |

* cited by examiner

NON-WOVEN OF SPUNBONDED THERMOPLASTIC FILAMENTS HAVING IMPROVED WELDABILITY PROPERTIES AND METHOD FOR MANUFACTURING SUCH A NON-WOVEN

TECHNICAL FIELD OF THE DISCLOSURE

The present disclosure relates to the technical field of non-wovens of spunbond thermoplastic filaments having improved weldability properties as well as to their manu-facturing method.

BACKGROUND OF THE DISCLOSURE

In the field of hygiene, in particular relating to diapers, protective pads or other equivalent means, non-wovens are generally provided to processors, who assemble them according to fastening areas with complementary materials, for example, superabsorbing materials or further tie ele-ments for forming said articles. The fastening areas, in particular with hygiene articles in mind, are subject to many forces when said articles are worn. It is therefore indispens-able that these fastening areas resist during the use of disposable hygiene articles.

With a concern of optimizing the manufacturing costs of such hygiene articles, in addition to optimized fastening rates, increasingly light non-wovens allowing the use of reduced amounts of polymers while providing satisfactory mechanical properties (tearing resistance, resistance to abra-sion, resistance to fluffing, weldability, . . . ) are particularly sought. The reduction of the surface mass of non-wovens gives the possibility of obtaining a less expensive web by reducing the transport, storage, production costs but also by reducing the amounts of waste, and thus finally obtaining less expensive diapers. As an example, the average mass of a disposable diaper for babies has passed from 65 g at the beginning of the 1980's to less than 42 g today (for any types of diaper and for any type of sizes), i.e. a reduction by 30%.

However, more the non-wovens have a low surface mass, less the fibers and/or filaments which make them up are distributed homogeneously in their structure, which gener-ates problems of reproducibility, of reliability of the resis-tance of the fastened areas, and in the presence of low mechanical strength areas.

Non-wovens may be assembled along fastening areas by a thermal weld, by ultrasound or further by high frequency welding.

Another technique for fastening non-wovens together, consists of assembling two non-woven webs by means of a thin layer of adhesive, notably a hot melt type adhesive. This technique however has the drawback that the adhesive layer has to remain confined between the two superposed non-wovens to be assembled and should not cross said non-wovens with the risk of changing the touch and aspect of the external faces of said non-wovens. When the non-woven is the external rear layer of a diaper, also designated in the state of the art under the term of «backsheet», it is superposed with a film impervious to liquids, which film is most often printed. The film impervious to liquids then forms an internal rear layer. This external rear or non-woven layer has the function of avoiding that the user touches the impervious plastic film and of ascribing an impression of comfort and softness to the diaper. In the latter case, if the adhesive passes through the non-woven covering film, the latter risks deteriorating the diaper. There exists a risk that the diapers adhere together, notably during packaging. This may be detrimental to the operation of the production line, as well as alter the primary function of the external rear layer also known under the term of backsheet. It is observed that the adhesive has a greater tendency of piercing through non-wovens having high perviousness, in particular concerning non-wovens having a low surface mass, i.e. of more than 35 g/m$^2$.

Indeed, the more the non-wovens have a low surface mass, the more increases their perviousness. The latter are thus more capable of being pierced through by a hot melt adhesive.

Document EP 2 028 296 B1 is known, disclosing a method for manufacturing a non-woven of spunbond filaments, also designated as a spunbond, relating to the application of a composition comprising two polypropylenes having differ-ent melt flow indexes, allowing the manufacturing of non-wovens having very thin filaments, in particular of less than 1 dtex. The obtained non-wovens have the drawbacks of having of medium weld resistance properties. It is actually observed that the thermobonded fastening areas of the articles comprising at least one of said non-wovens, for example hygiene articles such as diapers, tend to delaminate after the welding operation, in particular when the welding is carried out by means of a tool of the heat-sealing type.

OBJECT AND SUMMARY OF THE DISCLOSURE

The object of the present disclosure is thus, according to a first aspect, a non-woven having improved weldability properties, in particular having better homogeneity in the distribution of the filaments forming its structure while having improved mechanical strength and a low surface mass.

Said non-woven of spunbonded thermoplastic filaments comprises in a characteristic way at least 95% by mass (g) of its surface mass (g/m$^2$) of at least two polymers of polypropylene A and B, said filaments having a titer of less than or equal to 1.3 dtex, said non-woven having a surface mass of less than or equal to 35 g/m$^2$, the welding rate being at least 10% and at most 25%. Further, said non-woven comprises at least 88% by mass (g) of its surface mass (g/m$^2$) of said polypropylene polymer A obtained by polym-erization in the presence of at least one polymerization catalyst based on a metallocene and at most 12% by mass (g) of its surface mass of said polypropylene B polymer.

Surprisingly, the non-woven according to the disclosure has improved mechanical and thermal welding properties. By thermal welding is meant any welding made with addi-tional heat, and notably high frequency, ultrasonic welding or further by means of a tool heated by means of one or several electric resistors for example at temperatures com-prised between 80° C. and 160° C. The non-woven accord-ing to the disclosure may thus be advantageously assembled by using fastening machines applying upper and lower jaws heated by means of electric resistors and thus give the possibility of improving the assembling rates of the lami-nated articles comprising several non-wovens without being detrimental to the mechanical properties of said non-wo-vens.

The term of spun-bonded designates a non-woven called in the state of the art a spunbond and which is formed by extrusion of a molten plastic material in the form of fila-ments through the orifices of a die, said filaments are stretched, deposited on a webbing belt, and then bonded together, for example by calendering.

The term of spun-melted or spunmelt designates any non-woven comprising at least two non-wovens of spunbonded thermoplastic filaments (also designated as such in the present text) and at least one non-woven of melt-blown fibers (also designated in the present text as meltblown fibers).

The polymers of polypropylene A and B are homopolymers of propylene or copolymers of propylene and of other alpha-olefins. Examples of alpha-olefins which may be copolymerized comprise the alpha-olefins with 2 to 20 carbon atoms, such as ethylene, 1-butene, 1-pentene, 1-hexene, 1-octene, 1-decene, 3-methyl-1-butene, 3-methyl-1-pentene, 3-ethyl-1-pentene, 4-methyl-1-pentene and 4-methyl-1-hexene. Ethylene and 1-butene are preferred, in particular ethylene. Such alpha-olefins may be polymerized alone or as a combination of two or more.

By thermoplastic is meant any plastic material, in the case of the present disclosure, polypropylene polymers capable of melting under the action of heat or at the very least of sufficiently softening so as to be able to be transformed several times without any significant alteration of its mechanical properties.

By non-woven, is understood any web of randomly entangled fibers and/or filaments, unlike a woven fabric or a knit for example.

By machine direction is meant the direction of the non-woven corresponding to the direction in which it has been produced, generally with reference to its position on the conveyer belt during the consolidation step, in particular during calendering. The cross direction corresponds to the direction perpendicular to the machine direction.

The welding rate of a non-woven is the ratio of the partial surface corresponding to the area in which the fibers/filaments are bonded, in particular calendered, relatively to the total surface of said non-woven. Generally, the spun thermoplastic filament webs are bonded by calendering, the welding ratio therefore depends on the surface etching patterns of the cylinder intended for calendering.

This welding rate may thus be computed either from etchings appearing on the etched cylinder applied during calendering or from the finished non-woven. In the latter case, a flat scanner is used for scanning with a high resolution one of the two surfaces of said non-woven. A specific measurement method is described in document US 2012/0179125 in paragraphs [0222] and the following.

Ziegler-Natta polymerization catalysts for homopolymers or copolymers of propylene are well known to one skilled in the art. The polymerization mechanisms are for example described in «Encyclopedia of Polymer Science and Engineering», Volume 8, page 162, published par John Wiley and Sons, Inc. 1987.

The polypropylene polymers described hereafter as being obtained by polymerization in the presence of a metallocene catalyst are produced according to a so-called metallocene method. Such polypropylene polymers are marketed by Exxon Chemical Company under the trade name of Exxon Achieve™, by Total Petrochemicals under the brand of LUMICENE®, or further by Lyondell Basell under the name of METOCENE®.

The polypropylene polymer B may be obtained by polymerization in the presence of a polymerization catalyst based on a metallocene and/or Ziegler-Natta.

The polymers of polypropylene A and B are different, notably in that they have different melt flow indexes, MFI (Melt Flow Index) (A) and MFI (Melt Flow Index) (B), respectively, measured according to the ISO 1133 standard, condition L, at 230° C. and with 2.16 kg, for example MFI (B) is greater than MFI (A), in another example MFI (B) is at least 15 times greater than MFI (A).

According to some embodiments, the polypropylene A polymer has a melt flow index of at least 10 g/10 mins and at most 35 g/10 mins, and the polypropylene B polymer has a melt flow index of at least 600 g/10 mins and at most 3,000 g/10 mins, the melt flow index being determined according to the ISO 1133 standard, condition L, at 230° C. and with 2.16 kg.

For example, the non-woven according to the disclosure comprises at most 7% by mass based on its surface mass of the polypropylene B polymer, still for example between 3% and 6% by mass of its surface mass of the polypropylene B polymer.

In one alternative, said non-woven comprises at least 93% by mass of its surface mass of said polypropylene A polymer.

The inventors noticed that the increase in the amount of polypropylene A in the initial extrudable composition during the manufacturing of the non-woven according to the disclosure, and therefore finally found at least in a mass proportion with respect to its surface mass, of greater than or equal to 93%, gives the possibility of improving the mechanical properties, in particular its ultimate strengths in the cross and machine directions.

Further, this proportion of polypropylene A polymer combined with the polypropylene B polymer allows considerable improvement of the welding resistance properties of the non-woven according to the disclosure.

In an alternative, the filaments have a titer comprised between 0.01 dtex and 1.2 dtex, for example between 0.5 dtex and 1.1 dtex, in another example between 0.5 dtex and 1 dtex and in yet another example between 0.7 dtex and 1 dtex.

According to some embodiments, when the non-woven is used in the manufacturing of a hygiene article, in particular for diapers, and notably as an external rear layer or «backsheet», the filaments have a titer of less than or equal to 1.2 dtex, for example less than or equal to 1.1 dtex, in another example less than or equal to 1 dtex.

Advantageously, the composition of polypropylene A and B polymers according to the disclosure gives the possibility of obtaining very fine filaments, and therefore with a greater length of filaments per square meter than in a non-woven of the same surface mass but having filaments with a titer above 1.3 dtex.

In one alternative, the non-woven according to the disclosure has a surface mass of at least 5 g/m² and of at most 30 g/m², for example of at least 10 g/m² and of at most 25 g/m².

In an alternative, said non-woven comprises at least 9.5 km of filaments per m².

This length interval of filaments is calculated according to the titer of said filaments and the surface mass of the non-woven. This length interval of spunbonded filaments per gram of non-woven and per m² gives the possibility of obtaining resistances in the machine direction and in the cross direction for the non-woven which are clearly improved comparatively to a non-woven of the spunbonded type consisting of a single polypropylene polymer obtained by polymerization in the presence of a Ziegler-Natta polymerization catalyst. In an alternative, said non-woven has a perviousness (l/m²/s) measured according to the ISO 9237 standard from 1995 of less than 6,500 l/m²/s, for example less than 6,100 l/m²/s.

Advantageously, the non-woven according to the disclosure retains restricted perviousness. A non-exhaustive explanation would be that as the filaments are very fine, the number of km of filaments per $m^2$ increases compared with filaments of greater titer, thereby ensuring a good distribution of the filaments in the structure of the non-woven.

The object of the present disclosure according to a second aspect relates to an article comprising at least one first non-woven according to any of the previous embodiment alternatives, and at least one second non-woven comprising fibers and/or filaments based on a polypropylene polymer, said first and second non-wovens are secured together along at least one fastening area in which they are thermobonded.

Said second non-woven may be a non-woven of the spunbonded type, a spunmelt (i.e. comprising at least two spunbonds and a meltblown), a meltblown, a carded web, a thermo-welded web, a needled web, a spunlaced web or further a combination of the latter.

According to some embodiments, the second non-woven is a first non-woven.

Said article is for example disposable, and may be a hygiene article such as a diaper, a catamenial device, a device for adult incontinence, or further respiratory masks, surgical blouses or protective garments, overblouses, . . . requiring the use of at least one fastening area in which the fibers and/or filaments are thermobonded.

Said fastening area may be obtained by means of a thermoweld causing at least partial melting of the fibers/filaments in polypropylene: a thermoweld by means of a heat sealer, of ultrasonic welding, high frequency welding. By «thermo-bound», is meant the fact of binding a non-woven on itself or with another non-woven by providing sufficient heat for causing total or partial melting of the fibers/filaments in the fastening area.

Said fastening area may correspond to a limited area of both fastened faces and in contact with first and second non-wovens or at the whole surface of said faces in contact.

According to some embodiments, the weld is a thermal weld and the fastening area comprises fibers/filaments which are at least partly molten.

In one alternative, said fastening area of the article comprises at least two first non-wovens, for example at least four first non-wovens.

The object of the present disclosure, according to a third aspect, is a hygiene article such as a diaper, adapted so as to be worn around the waist of a wearer, having a longitudinal axis (L), and comprising:

a front layer pervious to liquids, a rear area impervious to liquids, and an absorbing layer positioned between the front and rear layers.

Advantageously the rear layer impervious to liquids comprises a polymeric film impervious to liquids oriented towards said wearer and a first non-woven according to any of the previous alternative embodiments.

The absorbing layer has the function of absorbing and of storing liquids. This absorbing layer consists of fluff and of super-absorbing polymers, which are cross-linked polymers which may absorb at least fifty times their weight of a 0.9% saline solution according to the test for measuring the retention capacity (EDANA 441.2-01). The polymeric film impervious to liquids is for example extruded-calendered and comprises one or several of the following preferably meltable polymers: polypropylene, polyethylene, polyamide, polyethylene terephthalate, polyurethane.

In one alternative, the polymeric film impervious to liquids and said first non-woven are assembled along at least one fastening area in which said film and said first non-woven are thermobonded.

Their fastening area is defined as described above.

In an alternative, said hygiene article comprises a tie element fastened with said first non-woven along a fastening area in which said tie element and said first non-woven are thermobonded.

Said fastening area is defined as described above.

The tie elements described in the present disclosure comprise along a portion of their internal faces, tying members, for example hooks (for example with the shape of a T, of mushrooms, etc.) capable of cooperating with their tie with tying loops formed with the fibers and/or filaments which are projected from the external face of the rear layer of the hygiene article.

In an alternative, the rear layer of the hygiene article comprises fastened front and rear portions along lateral fastening areas in which said front and rear portions are thermobonded.

Said lateral fastening areas are defined as described above with reference to at least one fastening area.

In one alternative, the rear layer comprises at least two first non-wovens according to any of the previous embodiment alternatives.

The object of the disclosure, according to a fourth aspect, is a method for manufacturing a non-woven of spun-bonded thermoplastic filaments according to one of the previous alternative embodiments, comprising the following steps:

a. Extruding through the orifices of a die a composition based on polypropylene comprising at least 95% by weight of its weight of a mixture of two polypropylene A and B polymers, the polypropylene A polymer being present at a content of at least 88% by weight based on the weight of said composition and having a melt flow index of at least 10 g/10 mins and at most 35 g/10 mins, and the polypropylene B polymer being present at a content of at most 12% by weight based on the weight of said composition and having a melt flow index of at least 600 g/10 mins and at most 3 000 g/10 mins, the melt flow index being determined according to the ISO 1133 standard, condition L, at 230° C. and 2.16 kg, b. Stretching and webbing the extruded filaments on a support, c. Consolidating said filaments, notably by calendering for forming a non-woven.

In a characteristic way, the polypropylene A is obtained by polymerization in the presence of a polymerization catalyst based on a metallocene.

The applicant noticed that this particular composition gives the possibility of obtaining a non-woven having improved behavior upon welding or of improving the behavior upon welding of a laminated article comprising at least one non-woven according to the disclosure and one or several different non-wovens, for example of the spunmelt type and this for non-wovens of small surface mass, notably less than or equal to 35 $g/m^2$. By improved behavior upon welding, is meant improvement of the resistance to delamination or to tearing of a fastening area comprising at least one non-woven according to the disclosure.

The composition according to the disclosure may comprise usual additives, such as antioxidants, anti-acids, anti-UVs, coloring agents, filler materials, antistatic agents, lubricating agents and slip-promoting agents. These additives are generally added by mixing them in the melt, for example during the manufacturing of the granules from the composition according to the disclosure. These granules are then melted with view to extrusion-spinning on an extrusion die for manufacturing a spunbonded non-woven web. The web is then consolidated for example by calendering. This operation consists of having the not yet consolidated web pass over a set of etched cylinders, for example heated, so as to generate inter-filamentary fastening areas and non-fastened areas for leaving loft and softness to said non-woven.

The total content of additives generally does not exceed 5% by weight of the total weight of the composition according to the disclosure; for example it is less than 2% by weight, and in another example less than 1% by weight.

According to some embodiments, the composition comprises at least 95% by weight of its weight of the mixture of the polypropylene A and B polymers, for example at least 98% by weight and in another example at least 99% by weight.

The indicated melt flow index within the scope of the present text is the one measured on the polypropylene polymer entering the composition according to the disclosure before its extrusion-spinning for manufacturing the non-woven.

In one alternative, the composition comprises at least 93% by weight of said polypropylene A polymer, and at most 7% by weight of said polypropylene B polymer, for example on the order of 3% to 6% by weight of said polypropylene B polymer.

In one alternative, the polypropylene B polymer is obtained by polymerization in the presence of a polymerization catalyst based on a metallocene and/or of Ziegler-Natta, for example a Ziegler-Natta catalyst.

In one alternative, the manufacturing method comprises the following steps for manufacturing an article according to any of the previous embodiment alternatives:

d. Superposing at least one first non-woven obtained at the end of step c), and a second non-woven, e. Fastening by means of a tool heated to a temperature comprised between 150° C. and 158° C., for example between 153° C. and 155° C., said at least two non-wovens along a fastening area in which said non-wovens are thermobonded.

The applicant determined that this temperature interval gives the possibility of improving resistance to delamination of the fastening area.

The second non-woven and the fastening area are defined above.

BRIEF DESCRIPTION OF THE DRAWINGS

The present disclosure will be better understood upon reading exemplary embodiments, mentioned in a non-limiting way, and the following figures wherein.

DETAILED DESCRIPTION

Figure 1:
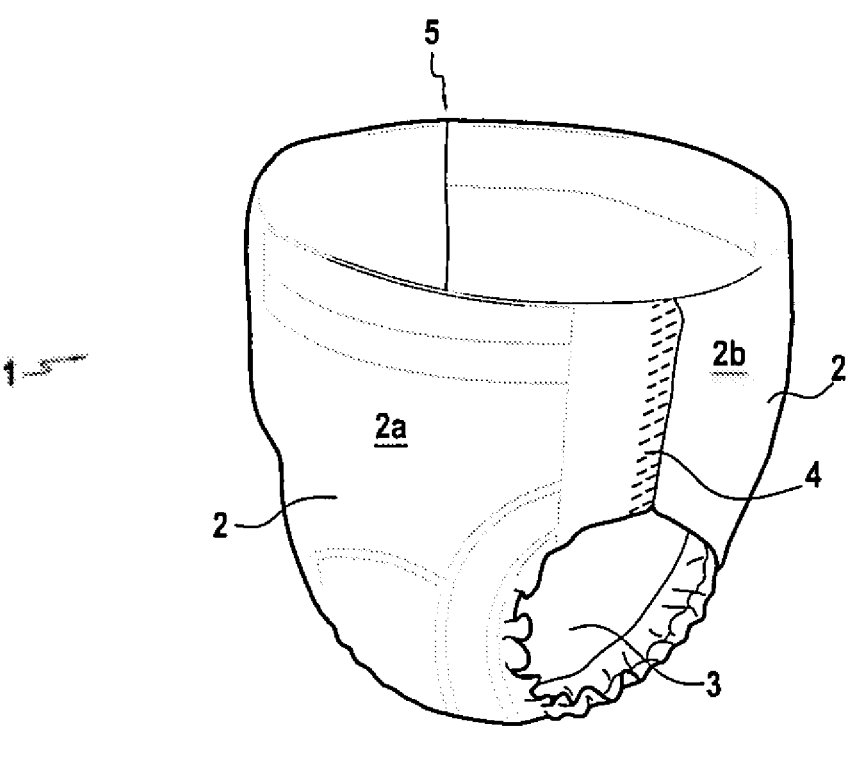
FIG. 1 schematically and in perspective illustrates a first alternative of a hygiene article, in particular a pull-up diaper, the rear layer of which comprises at least one non-woven according to the disclosure.

The diaper 1 illustrated in FIG. 1 is disposable and intended for babies. This diaper 1 comprises a rear layer 2 and a front layer 3 between which is positioned an absorbing layer. The rear layer 2 comprises at least two first non-wovens according to the disclosure. The front 2a and rear 2b portions of the rear layer 2 are fastened along lateral fastening areas 4 and 5 in which the filaments of polypropylene polymers are at least partly melted. This diaper 1 in the state of the art is also designated under the term of «training pant» and is positioned on the waist of the user by having his/her legs pass through both openings.

Figure 2:
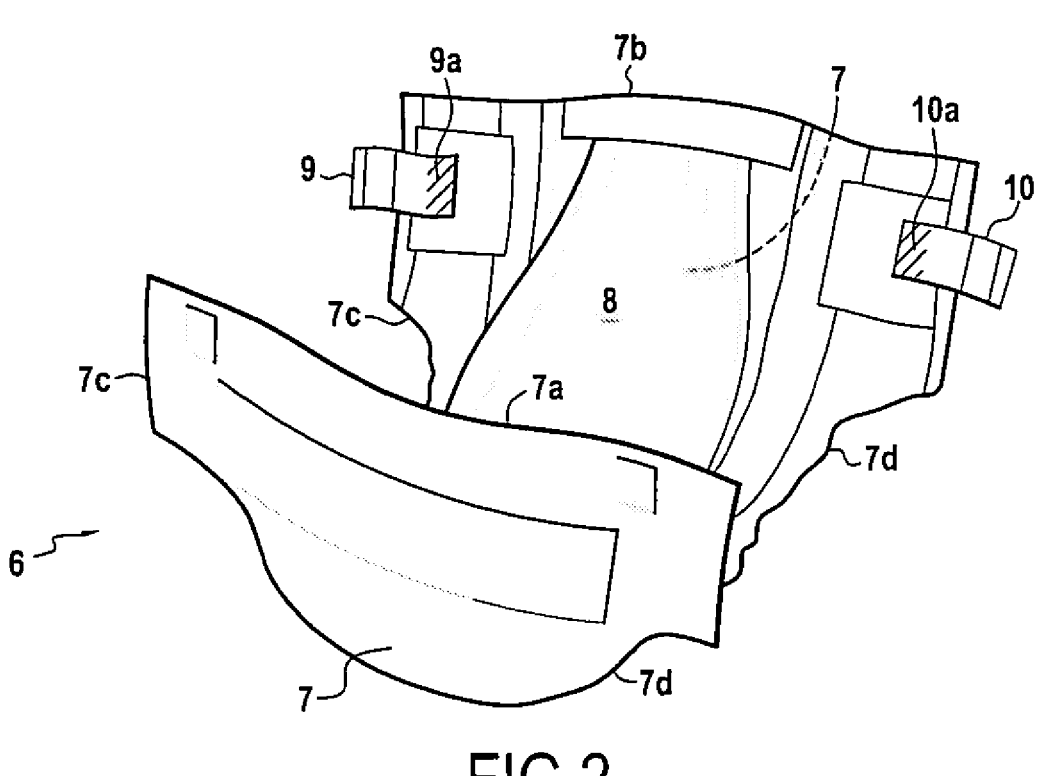
FIG. 2 schematically and in perspective illustrates a second alternative of a hygiene article, in particular a diaper wherein the rear layer comprises at least two non-wovens according to the disclosure.

The diaper 6 illustrated in FIG. 2 is also disposable and intended for babies. This diaper comprises a front layer 8 and a rear layer 7 between which an absorbing layer not shown is positioned. The rear layer 7 comprises at least one non-woven according to the disclosure, for example at least two non-wovens according to the disclosure. The front 7a, rear 7b and lateral 7c and 7d edges are for example assembled by providing heat, in particular by means of a heat sealer or by ultrasonic or high frequency welding. The diaper 6 also comprises two tie elements 9 and 10 fastened to the rear layer 7 along the fastening areas 9a and 10a by providing heat, and notably by means of a heat sealer, of ultrasonic waves or high frequencies.

The rear layer 7 comprises a film impervious to liquids and pervious to air as an internal rear layer and at least one non-woven according to the disclosure, for example at least two non-wovens according to the disclosure, covering said film and forming an external rear layer. The internal rear layer formed with a film impervious to liquids is oriented facing the wearer of the diaper 1 while the external rear layer formed with at least one non-woven according to the disclosure will come into contact with the person who places the diaper on the wearer.

Figure 3:
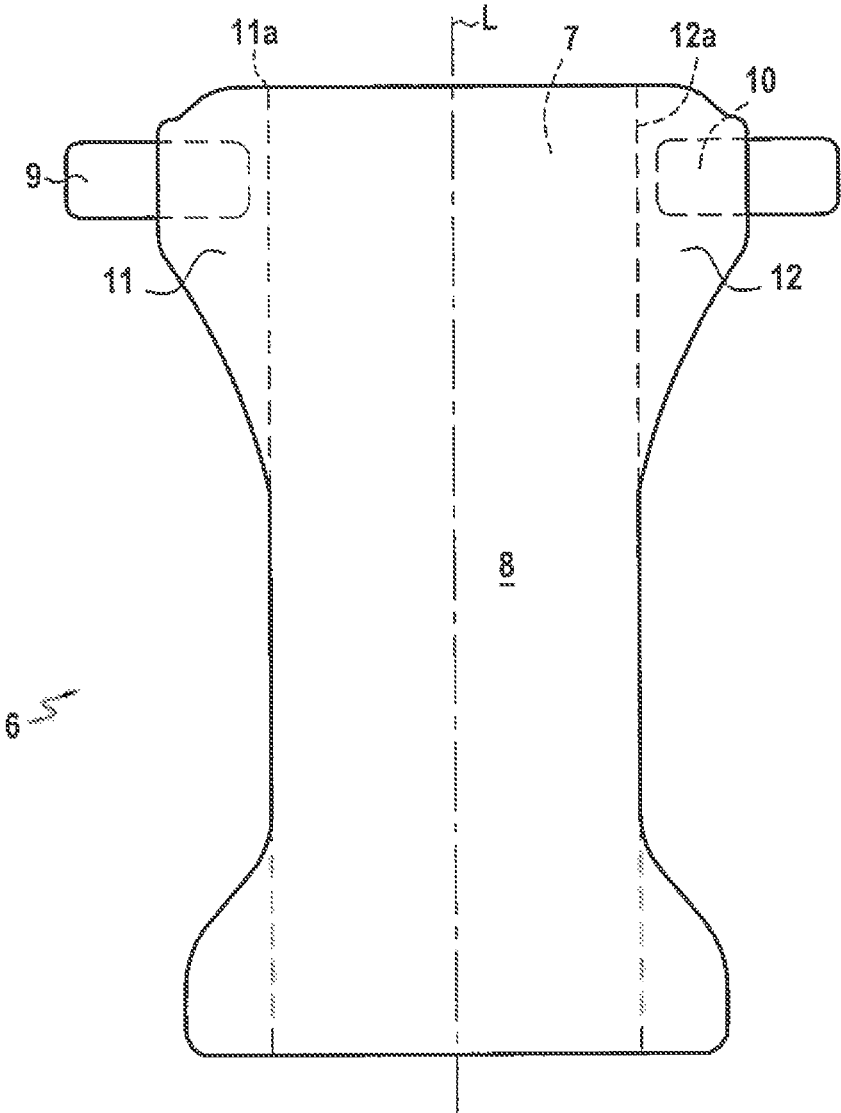
FIG. 3 schematically illustrates in a flat top view the hygiene article illustrated in FIG. 2.

In the alternative of the diaper 6 illustrated in FIG. 2, the tie elements 9 and 10 are directly fastened to the rear layer 7 but the latter may be fastened to intermediate tying tabs 11 and 12 delimited relatively to the rear layer 7 by dotted lines illustrated in FIG. 3. In the latter case, the intermediate tying tabs 11 and 12 are fastened along the fastening areas 11a and 12a by providing heat on the rear layer 7. The tie elements 9 and 10 as for them are fastened in the same way to the intermediate tying tabs 11 and 12 as to the rear layer 7. According to some embodiments of the disclosure, the intermediate tying tabs 11 and 12 comprise at least one non-woven according to the disclosure, preferably at least two non-wovens.

Tables 1 to 4 hereafter repeat the results of tests conducted on different spunbonded non-wovens according to the disclosure and to the state of the art, and on the articles combining them.

TABLE 1

| Welding parameters | Example 1/ Breakage Force | Example 2/ Breakage Force | Example 3/ Breakage Force | Example 4/ Breakage Force | Example 5/ Breakage Force | Example 6/ Breakage Force | Example 7/ Breakage Force | Example 8/ Breakage Force |
|---|---|---|---|---|---|---|---|---|
| T ° C.: 150° C. Force: 150 N (=3 bars) Time: 1 second | 8.6 N/5 cm | 8.3 N/5 cm | 8.8 N/5 cm | 4.5 N/5 cm | 13 N/5 cm | 7.8 N/5 cm | 10.5 N/5 cm | 3.2 N/5 cm |

TABLE 1-continued

| Welding parameters | Example 1/ Breakage Force | Example 2/ Breakage Force | Example 3/ Breakage Force | Example 4/ Breakage Force | Example 5/ Breakage Force | Example 6/ Breakage Force | Example 7/ Breakage Force | Example 8/ Breakage Force |
|---|---|---|---|---|---|---|---|---|
| T ° C.: 153° C. Force: 150 N (=3 bars) Time: 1 second | 15 N/5 cm | 15.1 N/5 cm | 17 N/5 cm | 6.7 N/5 cm | 35 N/5 cm | 29 N/5 cm | 29.3 N/5 cm | 5.4 N/5 cm |
| T ° C.: 155° C. Force: 150 N (=3 bars) Time: 1 second | 22.6 N/5 cm | 25.5 N/5 cm | 27.3 N/5 cm | 12.1 N/5 cm | 56.1 N/5 cm | 50.7 N/5 cm | 47.5 N/5 cm | 14.8 N/5 cm |

Example 1 is an article comprising a spunbond according to the disclosure of 16 g/m² (designated in the continuation of the present text as a mixed polymer spunbond) obtained by applying the composition according to the disclosure comprising a mixture of two polypropylene A and B polymers, the polypropylene A polymer being present at a content of at least 93% by weight based on the weight of said composition, in this specific example on the order of 95% by weight, and having a melt flow index of 27 g/10 mins and the polypropylene B polymer being present at a content of at most 7% by weight based on the weight of said composition, in this specific example about 5% by weight, and having a melt flow index of 1,200 g/10 mins. Said article also comprises, superposed in this order on the mixed polymer spunbond of 16 g/m², two spun melts (spunbond/meltblown/spunbond) each of 15 g/m² and a mixed polymer spunbond of 16 g/m². The four layers of non-wovens were individually calendered by means of an etched and heated cylinder so that the ratio of the surface area of the welded areas based on the surface area of the non-wovens is less than or equal to 25%, for example on the order of 20%. The patterns of the etching are T-shaped for the mixed polymer spunbond. According to some embodiments, the polypropylene A and B polymers in said composition are homopolymers. The surface mass of the obtained article is 62 g/m². The mixed polymer spunbonds have in this specific example filaments having a titer of 1.17 dtex to within more or less 5% on average. The spunbond of the spun melt comprises filaments having a titer of 1.7 dtex and fibers of about 2 μm for the meltblown. In the present text, the fibers of the meltblown non-wovens have a diameter of about 2 μm and a titer of 0.03 dtex.

Examples 2 to 21 are described by their differences with Example 1, they also have a welding rate from 16 to 22%.

Example 2 is an article of 62 g/m² comprising in this order, superposed, a mixed polymer spunbond of 16 g/m² (1.08 dtex/filaments), two spun melts of 15 g/m² each (1.89 dtex/filament/spunbond), and a mixed polymer spunbond of 16 g/m² (1.08 dtex/filament). The patterns of the etching are diamond tips for the mixed polymer spunbonds.

Example 3 is an article of 66 g/m² comprising within this order, superposed, a mixed polymer spunbond of 18 g/m² (1.09 dtex/filament), two spun melts of 15 g/m² each (1.89 dtex/filament/spunbond), and a mixed polymer spunbond of 18 g/m² (1.09 dtex/filament). The patterns of the etching are diamond tips for the mixed polymer spunbonds.

Example 4 is an article of 70 g/m² comprising in this order, superposed, a standard spunbond of 20 g/m² (2.11 dtex/filament), two spun melts of 15 g/m² each (1.89 dtex/filament/spunbond), a standard spunbond of 20 g/m² (2.11 dtex/filament). The patterns of the etching are T-shaped for the standard spunbond.

Example 5 is an article of 64 g/m² comprising four mixed polymer spunbonds of 16 g/m² each (1.17 dtex/filament). The patterns of the etching being T-shaped.

Example 6 is an article of 64 g/m² comprising four mixed polymer spunbonds of 16 g/m² each (1.08 dtex/filament). The patterns of the etching are diamond tips.

Example 7 is an article of 72 g/m² comprising four mixed polymer spunbonds of 18 g/m² each (1.09 dtex/filament). The patterns of the etching are diamond tips.

Example 8 is an article of 80 g/m² comprising four standard spunbonds of 20 g/m² each (2.11 dtex/filament). The welding patterns are Ts.

The first column of Table 1 indicates the welding parameters for Examples 1 to 8. The articles described in Examples 1 to 8 have thus been welded along a given fastening area by means of a welder comprising heated upper and lower jaws. The temperatures of the jaws are indicated in the first column as well as the pressures exerted by both jaws, and the welding time (which is always one second).

The breakage resistances in Newtons/5 cm indicated in the remaining columns of Table 1 result from the average of three tensile breakage tests conducted on either side of said fastening area. Both fastened portions of the articles being projected on either side of the fastening area, are positioned between the upper and lower jaws of a traction bench of the Lloyd type and distant by 10 cm. The traction speed is 300 mm/min. The four tested non-wovens have a width of 50 mm and a length of 200 mm. The welding machine used is a OTTO BRUGGER HSG/C heat sealer.

Upon reading the results appearing in Table 1, it is observed that the breakage force of the fastening area is improved from the moment that the article comprises at least one spunbond filament non-woven according to the disclosure as compared with articles comprising standard spunbonds, and this regardless of the temperature at which the four layers of non-wovens are welded in said area. This breakage force is improved when the article comprises two mixed polymer spunbond non-wovens, and further improved when it comprises four mixed polymer spunbonds non-wovens, and always regardless of the temperature at which the four non-wovens are assembled in said area.

It is also noted that the temperature at which the fastening area is formed has an influence on the obtained breakage force. For example the breakage force (N/5 cm) is multiplied by three for the article of Example 6 between 150° C. and 153° C., and multiplied by five between 150° C. and 155° C.

TABLE 2

| Welding parameters | Example 9/ Breakage Force | Example 10/ Breakage Force | Example 11/ Breakage Force | Example 12/ Breakage Force |
|---|---|---|---|---|
| T ° C.: 150° C. Force: 150 N (=3 bars) Time: 1 second | 15.7 N/5 cm | 2.7 N/5 cm | 7.8 N/5 cm | 4.3 N/5 cm |
| T ° C.: 153° C. Force: 150 N (=3 bars) Time: 1 second | 40.4 N/5 cm | 7.2 N/5 cm | 29 N/5 cm | 6.7 N/5 cm |
| T ° C.: 155° C. Force: 150 N (=3 bars) Time: 1 second | 28.9 N/5 cm | 20.4 N/5 cm | 50.7 N/5 cm | 13.8 N/5 cm |
| T ° C.: 158° C. Force: 150 N (=3 bars) Time: 1 second | — | 25.6 N/5 cm | 60.2 N/5 cm | 24.4 N/5 cm |

Example 9 is an article of 60 g/m$^2$ comprising four spunbond non-wovens of 15 g/m$^2$ (2.44 dtex/filament), consisting in a composition comprising a single polypropylene polymer obtained by polymerization in the presence of a metallocene polymerization catalyst, in this specific example, this is the polypropylene A polymer.

Example 10 is an article of 60 g/m$^2$ comprising four spunbond non-wovens of 15 g/m$^2$ (2.4 dtex/filament), each consisting in a composition comprising a single polypropylene polymer obtained by polymerization in the presence of a Ziegler-Natta polymerization catalyst.

Example 11 is an article of 64 g/m$^2$ comprising four non-wovens (1.08 dtex/filament) according to the disclosure (mixed polymer spunbond) in particular each consisting in a composition comprising the polymer A and the polymer B.

Example 12 is an article of 60 g/m$^2$ comprising four spunmelt non-wovens in particular each non-woven is a web of the SMS (Spunbond/Meltblown/Spunbond) type of 15 g/m$^2$ (1.89 dtex/filament/spunbond) each consisting in a composition comprising a single polypropylene polymer obtained by polymerization in the presence of a Ziegler-Natta polymerization catalyst.

The welding parameters of the fastening area of the laminated articles of Examples 9 and 12 are the same as those described for Examples 1 to 8.

Upon reading Table 2, it is observed that the article of Example 9 does not resist to a welding temperature of 158° C. since the article is totally melted in contact with the jaws of the heat sealer. Thus, the use of a single polypropylene A polymer for manufacturing a spunbond non-woven does not give the possibility of obtaining high and reproducible breakage forces, it is necessary to also use a polypropylene B polymer selected according to the disclosure.

The articles of Examples 10 and 12 resist to a welding temperature of 158° C. but do not give the possibility of obtaining breakage forces as high as those obtained for Example 11 comprising four non-wovens according to the disclosure.

TABLE 3

| Measured parameters | Example 13 | Example 14 | Example 15 |
|---|---|---|---|
| Breakage force (Newtons)/ machine direction WSP 110.4(09) | 37 N/5 cm | 25 N/5 cm | 27.5 N/5 cm |
| Breakage force (Newtons)/ cross direction WSP 10.4 (09) | 22.6 N/5 cm | 14.6 N/5 cm | 17.7 N/5 cm |
| Elongation (%) in the same machine direction WSP 110.4 (09) | 75% | 50.1% | 77.7% |
| Elongation (%) in the cross direction WSP 110.4 (09) | 84.5% | 52.9% | 80.7% |
| Titer of a filament (dtex) | 1.05 dtex | 1.15 dtex | 2 dtex |
| Perviousness to air (l/m$^2$/s) ISO 9237 standard | 5100 l/m$^2$/s | 5900 l/m$^2$/s | 7400 l/m$^2$/s |
| Length of filaments per m$^2$ in kilometers | 114 | 104 | 60 |

Example 13 corresponds to a mixed polymer spunbond non-woven according to the disclosure of 12 g/m$^2$, the weight proportion of the polypropylene A and B polymers of which is 95% and 5% respectively based on the weight of the extrudable composition according to the disclosure. The proportions of additives on the order of 0.5% to 1% by weight based on the weight of said compositions were not counted.

Example 14 corresponds to a mixed polymer spunbond non-woven of 12 g/m$^2$ the weight proportion of polypropylene A and B polymers of which is 90% and 10% respectively within the composition according to the disclosure. The proportions of additives of the order of 0.5% to 1% by weight based on the weight of said composition were not counted.

Example 15 corresponds to a standard non-woven of 12 g/m$^2$ (a single polypropylene polymer obtained by polymerization in the presence of a Ziegler-Natta polymerization catalyst).

It is observed that the more the amount of polypropylene A increases, the more the titer of the filaments decreases. Correlatively, the length of the filaments in kilometers per m$^2$ of non-woven also increases.

Advantageously, it is observed that Examples 13 and 14 also have a lower perviousness to air at equal weight as compared with Example 15. The breakage forces in the machine and cross directions are clearly improved for Example 13 as compared with Examples 14 and 15.

TABLE 4

| Welding parameters | Example 16/ Breakage force | Example 17/ Breakage force | Example 18/ Breakage force | Example 19/ Breakage force | Example 20/ Breakage force | Example 21/ Breakage force |
|---|---|---|---|---|---|---|
| T ° C.: 150° C. Force: 150 N (=3 bars) Time: 1 second | 3.1 N/5 cm | 9.7 N/5 cm | 17.4 N/5 cm | 13.9 N/5 cm | 11.9 N/5 cm | 15.1 N/5 cm |

TABLE 4-continued

| Welding parameters | Example 16/ Breakage force | Example 17/ Breakage force | Example 18/ Breakage force | Example 19/ Breakage force | Example 20/ Breakage force | Example 21/ Breakage force |
|---|---|---|---|---|---|---|
| T ° C.: 153° C.<br>Force: 150 N<br>(=3 bars)<br>Time: 1 second | 5.6 N/5 cm | 24.5 N/5 cm | 28.1 N/5 cm | 21.9 N/5 cm | 44 N/5 cm | 41.4 N/5 cm |
| T ° C.: 155° C.<br>Force: 150 N<br>(=3 bars)<br>Time: 1 second | — | — | — | — | 54.9 N/5 cm | 28.4 N/5 cm |
| T ° C.: 158° C.<br>Force: 150 N<br>(=3 bars)<br>Time: 1 second | — | — | — | — | 35 N/5 cm | 26.2 N/5 cm |

Examples 16 to 21 are described by their differences with Example 1 and tested in the same way as regards the breakage force of the fastening area, as for Example 1. The proportions of additives of the order of 0.1 to 0.5% by weight based on the weight of the extrudable composition were not counted in the values given in Examples 16 to 21.

Example 16 is an article of 40 g/m² comprising four mixed polymer spunbond non-wovens of 10 g/m² (0.97 dtex/filament) according to the disclosure, the extrudable composition comprises 90% by weight of its weight of a polypropylene A polymer obtained by polymerization in the presence of a Ziegler-Natta polymerization catalyst and 10% by weight of a polypropylene B polymer obtained by polymerization in the presence of a Ziegler-Natta polymerization catalyst.

Example 17 is an article of 40 g/m² comprising four mixed polymer spunbond non-wovens of 10 g/m² (0.81 dtex/filament), the extrudable composition comprises 90% by weight of its weight of a polypropylene A polymer obtained by polymerization in the presence of a polymerization catalyst based on a metallocene and 10% by weight of its weight of a polypropylene B polymer obtained by polymerization in the presence of a Ziegler-Natta polymerization catalyst.

Example 18 is an article of 40 g/m² comprising four mixed polymer spunbond non-wovens of 10 g/m² (1.02 dtex/filament), the extrudable composition comprises 95% by weight of its weight of a polypropylene A polymer obtained by polymerization in the presence of a polymerization catalyst based on a metallocene and 5% by weight of its weight of a polypropylene B polymer obtained by polymerization in the presence of a Ziegler-Natta polymerization catalyst.

Example 19 is an article of 40 g/m² comprising four mixed polymer spunbond non-wovens of 10 g/m² (1.17 dtex/filament), the extrudable composition comprises 90% by weight of its weight of a polypropylene A polymer obtained by polymerization in the presence of a polymerization catalyst based on a metallocene and 10% by weight of its weight of a polypropylene B polymer obtained by polymerization in the presence of a Ziegler-Natta polymerization catalyst.

Example 20 is an article of 64 g/m² comprising four mixed polymer spunbond non-wovens of 16 g/m² (1.02 dtex/filament), the extrudable composition comprises 95% by weight of its weight of a polypropylene A polymer obtained by polymerization in the presence of a polymerization catalyst based on a metallocene and 5% by weight of its weight of a polypropylene B polymer obtained by polymerization in the presence of a Ziegler-Natta polymerization catalyst. The patterns of the etching are T-shaped.

Example 21 is an article of 64 g/m² comprising four mixed polymer spunbond non-wovens of 16 g/m² (1.03 dtex/filament), the extrudable composition comprises 90% by weight of its weight of a polypropylene A polymer obtained by polymerization in the presence of a polymerization catalyst based on a metallocene and 10% by weight of its weight of a polypropylene B polymer obtained by polymerization in the presence of a Ziegler-Natta polymerization catalyst. The patterns of the etching are diamond tips.

The difference between the breakage forces obtained for welds between Examples 16 and 17 demonstrate very clearly that the selection of a polypropylene A polymer obtained by polymerization in the presence of a catalyst based on metallocene gives the possibility of very significantly improving the resistance of the obtained fastening areas and this regardless of the temperature of the weld as compared with the use of the polypropylene A polymer obtained by polymerization in the presence of a Ziegler-Natta polymerization catalyst.

The results of the breakage forces obtained for Examples 18 and 19 give the possibility of demonstrating the improvement in the resistance of the fastening area for an extrudable composition comprising about 95% by weight of its weight of a polypropylene A polymer (metallocene) as compared with an extrudable composition comprising about 90% by weight of its weight of said polymer A.

Finally, Examples 20 and 21 clearly demonstrate that the breakage force obtained for the fastening area is further improved by selecting the fastening temperature, in particular between 153° C. and 155° C.

Throughout the description, including the claims, the term "comprising a" should be understood as being synonymous with "comprising at least one" unless otherwise stated. In addition, any range set forth in the description, including the claims should be understood as including its end value(s) unless otherwise stated. Specific values for described elements should be understood to be within accepted manufacturing or industry tolerances known to one of skill in the art, and any use of the terms "substantially" and/or "approximately" and/or "generally" should be understood to mean falling within such accepted tolerances.

Where any standards of national, international, or other standards body are referenced (e.g., ISO, etc.), such references are intended to refer to the standard as defined by the national or international standards body as of the priority date of the present specification, unless otherwise explicitly specified herein. Any subsequent substantive changes to such standards are not intended to modify the scope and/or definitions of the present disclosure and/or claims.

It is intended that the specification and examples considered as exemplary only, with a true scope of the disclosure being indicated by the following claims.

The invention claimed is:

1. A non-woven of spunbonded thermoplastic filaments comprising a polymeric mixture, the polymeric mixture consists of a combination of (i) at least 88% by weight of polypropylene A polymer and (ii) from 3 to 12% by weight of a polypropylene B polymer, wherein said non-woven comprises at least 95% by mass (g) of it surface mass (g/m²) of at least the combination of (i) the polypropylene A polymer and (ii) the polypropylene B polymer, said filaments having a titer of from 1.0 dtex to less than or equal to 1.3 dtex, said non-woven having a surface mass of less than or equal to 35 g/m², a welding rate being at least 10% and at most 25%, wherein said polypropylene A polymer is obtained by polymerization in the presence of at least one polymerization catalyst based on metallocene and said polypropylene B polymer is obtained by polymerization in the presence of a Ziegler-Natta catalyst, wherein said polypropylene A polymer comprises a first melt flow index that is at least 10 g/10 mins and at most 35 g/10 mins according to ISO 1133 standard, condition L, at 230° C. and with 2.16 kg, and said polypropylene B polymer comprises a second melt flow index that is at least 600 g/10 mins and at most 3,000 g/10 mins according to ISO 1133 standard, condition L, at 230° C. and with 2.16 kg; wherein a ratio between the second melt flow index and the first melt flow index is from 86:1-300:1, and wherein the polypropylene A polymer is a first homopolymer of polypropylene and the polypropylene B polymer is a second homopolymer of polypropylene;

wherein the non-woven is thermally bondable at a bonding temperature from 150° C. to 160° C., and wherein the non-woven has a machine-direction elongation from 50.1% to 75% at break as determined by WSP 110.4(09); and wherein the non-woven has a perviousness (l/m²/s) measured according to the ISO 9237 standard from 1995 of less than 6,500 l/m²/s.

2. The non-woven according to claim 1, wherein said non-woven comprises at least 93% by mass of its surface mass of said polypropylene A polymer.

3. The non-woven according to claim 1, wherein the filaments have a titer comprised between 1.0 dtex and 1.2 dtex.

4. The non-woven according to claim 1, wherein said non-woven has a surface mass of at least 5 g/m² and of at most 30 g/m².

5. The non-woven according to claim 4, wherein said non-woven has a surface mass of at least 10 g/m² and at most 25 g/m².

6. The non-woven according to claim 1, wherein said non-woven comprises 9.5 km of filaments per m².

7. The non-woven according to claim 1, wherein said non-woven has a perviousness (l/m²/s) measured according to the ISO 9237 standard dating from 1995 of less than 6,100 l/m²/s.

8. An article comprising at least one first non-woven according to claim 1, and at least one second non-woven comprising fibers and/or filaments based on a polypropylene polymer, said first non-woven and said second non-woven are thermobonded to each other along at least one fastening area.

9. The article according to claim 8, wherein said fastening area comprises at least two first non-wovens.

10. The article according to claim 9, wherein said fastening area comprises at least four first non-wovens.

11. The non-woven according to claim 1, wherein the second melt flow index comprises at least 1200 g/10 mins and at most 3,000 g/10 mins according to ISO 1133 standard, condition L, at 230° C. and with 2.16 kg.

12. The non-woven according to claim 1, wherein the non-woven has a first breakage-force-to-percent-elongation ratio in a machine direction of 0.5; wherein a machine direction breakage force has units of Newtons per 5 cm (N/5 cm) as determined according to WSP 110.4(09) and the machine direction elongation is determined according to WSP 110.4(09).

13. The non-woven according to claim 12, wherein the non-woven has a second breakage-force-to-percent-elongation ratio in a cross-direction from 0.28 to 0.3; wherein a cross-direction breakage force has units of Newtons per 5 cm (N/5 cm) as determined according to WSP 110.4(09) and the cross-direction elongation is determined according to WSP 110.4(09).

14. The non-woven according to claim 13, wherein a weight ratio between the polypropylene A polymer and the polypropylene B polymer is from 90:10 to 95:5.

15. The non-woven according to claim 1, wherein the non-woven has a percent elongation ratio between a machine direction elongation and a cross-direction elongation from 0.88 to 0.94 as determined according to WSP 110.4(09).

16. The non-woven according to claim 1, wherein the ratio between the second melt flow index and the first melt flow index is from 86:1-120:1.

17. The non-woven according to claim 1, wherein the ratio between the second melt flow index and the first melt flow index is from 120:1-300:1.

18. A non-woven of spunbonded thermoplastic filaments consisting of a polymeric mixture, the polymeric mixture consists of a combination of (i) at least 88% by weight of polypropylene A polymer and (ii) from 3 to 12% by weight of a polypropylene B polymer, wherein said non-woven comprises at least 95% by mass (g) of it surface mass (g/m²) of at least the combination of (i) the polypropylene A polymer and (ii) the polypropylene B polymer, said filaments having a titer of from 1.0 dtex to less than or equal to 1.3 dtex, said non-woven having a surface mass of less than or equal to 35 g/m², a welding rate being at least 10% and at most 25%, wherein said polypropylene A polymer is obtained by polymerization in the presence of at least one polymerization catalyst based on metallocene and said polypropylene B polymer is obtained by polymerization in the presence of a Ziegler-Natta catalyst, wherein said polypropylene A polymer comprises a first melt flow index that is at least 10 g/10 mins and at most 35 g/10 mins according to ISO 1133 standard, condition L, at 230° C. and with 2.16 kg, and said polypropylene B polymer comprises a second melt flow index that is at least 600 g/10 mins and at most 3,000 g/10 mins according to ISO 1133 standard, condition L, at 230° C. and with 2.16 kg; wherein a ratio between the second melt flow index and the first melt flow index is from 86:1-300:1, and wherein the polypropylene A polymer is a first homopolymer of polypropylene and the polypropylene B polymer is a second homopolymer of polypropylene;

wherein the non-woven is thermally bondable at a bonding temperature from 150° C. to 160° C., and wherein 5 the non-woven has a machine-direction elongation from 50.1% to 75% at break as determined by WSP 110.4(09); and wherein the non-woven has a perviousness $(l/m^2/s)$ measured according to the ISO 9237 standard from 1995 of less than 6,500 $l/m^2/s$. 10

\* \* \* \* \*